United States Patent
Fukushima (12)

(10) Patent No.: US 10,209,226 B2
(45) Date of Patent: Feb. 19, 2019

(54) PHOTOACOUSTIC MICROSCOPE APPARATUS

(71) Applicant: OLYMPUS CORPORATION, Tokyo (JP)

(72) Inventor: Ikutoshi Fukushima, Fuchu (JP)

(73) Assignee: OLYMPUS CORPORATION, Tokyo (JP)

(*) Notice: Subject to any disclaimer, the term of this patent is extended or adjusted under 35 U.S.C. 154(b) by 172 days.

(21) Appl. No.: 15/248,341

(22) Filed: Aug. 26, 2016

(65) Prior Publication Data

US 2016/0363563 A1 Dec. 15, 2016

Related U.S. Application Data

(63) Continuation of application No. PCT/JP2015/050292, filed on Jan. 7, 2015.

(30) Foreign Application Priority Data

Feb. 26, 2014 (JP) ................. 2014-035423

(51) Int. Cl.
*G01N 29/24* (2006.01)
*G02B 26/10* (2006.01)
(Continued)

(52) U.S. Cl.
CPC ....... *G01N 29/2418* (2013.01); *A61B 5/0095* (2013.01); *G01N 29/0681* (2013.01);
(Continued)

(58) Field of Classification Search
CPC .......... G01N 29/2418; G01N 29/0681; G01N 29/0672; G01N 21/008; G01N 21/06;
(Continued)

(56) References Cited

U.S. PATENT DOCUMENTS 4,267,732 A 5/1981 Quate
4,407,008 A * 9/1983 Schmidt ............. G01N 21/1702
348/79
(Continued)

FOREIGN PATENT DOCUMENTS

CN 102944521 A 2/2013
JP S60-049254 B2 10/1985
(Continued)

OTHER PUBLICATIONS

International Search Report dated Apr. 14, 2015 issued in corresponding International Patent Application No. PCT/JP2015/050292.
(Continued)

*Primary Examiner* — Helen C Kwok
(74) *Attorney, Agent, or Firm* — Scully, Scott, Murphy & Presser, P.C.

(57) ABSTRACT

A photoacoustic microscope apparatus includes a light source that emits excitation light which generates photoacoustic waves, an objective lens which focuses the excitation light on a specimen, a scanning unit which moves a focused position of the excitation light on the specimen, a photoacoustic-wave detecting unit which has a sensor unit that detects a photoacoustic wave generated, and an image constructing unit which constructs an image based on data from the photoacoustic-wave detecting unit. For the sensor unit, an angle of a range which is capable of receiving the photoacoustic wave incident on the sensor unit is larger than an angle corresponding to a numerical aperture on a side illuminated of the objective lens.

14 Claims, 12 Drawing Sheets

(51) Int. Cl.
  *G02B 21/00* (2006.01)
  *A61B 5/00* (2006.01)
  *G01N 29/06* (2006.01)
  *G02B 21/06* (2006.01)

(52) U.S. Cl.
  CPC ......... *G02B 21/002* (2013.01); *G02B 21/008* (2013.01); *G02B 21/0028* (2013.01); *G02B 21/0048* (2013.01); *G02B 21/06* (2013.01); *G02B 26/105* (2013.01)

(58) Field of Classification Search
  CPC .............. G01N 21/4795; G02B 21/002; G02B 21/0028; G02B 21/0048; G02B 21/0056; G02B 21/0072
  See application file for complete search history.

(56) References Cited

U.S. PATENT DOCUMENTS

| | | | | |
|---|---|---|---|---|
| 4,893,008 A * | 1/1990 | Horikawa | .......... | G01N 21/6458 250/234 |
| 5,037,180 A * | 8/1991 | Stone | ................ | G02B 6/02052 359/890 |
| 5,062,715 A * | 11/1991 | Nakata | ............... | G01N 29/2418 356/432 |
| 5,208,648 A * | 5/1993 | Batchelder | ......... | G01N 21/9505 356/237.1 |
| 5,214,282 A * | 5/1993 | Yamaguchi | ............ | B82Y 20/00 250/306 |
| 5,781,294 A * | 7/1998 | Nakata | ............... | G01N 21/1702 356/487 |
| 6,428,171 B1 * | 8/2002 | Aoki | ................. | G01B 11/0608 250/559.38 |
| 7,236,251 B2 * | 6/2007 | Takaoka | ............. | G01N 21/4795 356/479 |
| 8,896,842 B2 * | 11/2014 | Bower | .................. | A61B 3/102 356/497 |
| 9,335,253 B2 | 5/2016 | Ode | | |
| 9,833,148 B2 * | 12/2017 | Wang | .................. | A61B 5/0095 |
| 2002/0048025 A1 | 4/2002 | Takaoka | | |
| 2004/0196466 A1 * | 10/2004 | Yamaguchi | .......... | G01N 21/171 356/432 |
| 2007/0187632 A1 * | 8/2007 | Igarashi | ............... | A61B 5/0048 250/559.36 |
| 2010/0268042 A1 * | 10/2010 | Wang | ................... | A61B 5/0059 600/322 |
| 2012/0204648 A1 * | 8/2012 | Wang | ................... | A61B 5/0095 73/606 |
| 2013/0197343 A1 | 8/2013 | Miyasato | | |
| 2013/0245406 A1 | 9/2013 | Wang et al. | | |
| 2014/0118749 A1 | 5/2014 | Nakajima et al. | | |
| 2015/0051497 A1 * | 2/2015 | Carver | ................ | A61B 5/0071 600/476 |
| 2015/0085296 A1 * | 3/2015 | Ode | ................... | G01N 29/0672 356/479 |
| 2015/0316510 A1 * | 11/2015 | Fukushima | .......... | G02B 21/002 73/643 |
| 2016/0081558 A1 | 3/2016 | Wang et al. | | |
| 2016/0113507 A1 * | 4/2016 | Reza | ................... | G01N 21/1717 356/477 |
| 2016/0150968 A1 * | 6/2016 | Imai | ..................... | A61B 5/0095 600/407 |
| 2016/0305912 A1 * | 10/2016 | Murayama | ........... | G01N 29/032 |

FOREIGN PATENT DOCUMENTS

| | | |
|---|---|---|
| JP | 2005-175919 A | 6/2005 |
| JP | 2011-519281 A | 7/2011 |
| JP | 2013-022127 A | 2/2013 |
| JP | 2013-255707 A | 12/2013 |
| JP | 2014-002318 A | 1/2014 |
| WO | 2013/108375 A1 | 7/2013 |
| WO | 2013/190843 A1 | 12/2013 |

OTHER PUBLICATIONS

Written Opinion of the International Searching Authority dated Apr. 14, 2015 issued in corresponding International Patent Application No. PCT/JP2015/050292.

Ryan L. Shelton, "Ultrahigh resolution photoacoustic microscopy via transient absorption", Biomedical Optics Express, Aug. 23, 2010, vol. 1, No. 2, pp. 676-686.

English translation of International Preliminary Report on Patentability dated Sep. 9, 2016 together with the Written Opinion received in related International Application No. PCT/JP2015/050292.

Japanese Office Action dated Dec. 6, 2017 in Japanese Patent Application No. 2014-035423.

Chinese Office Action dated Aug. 10, 2018 in Chinese Patent Application No. 201580003425.0.

\* cited by examiner

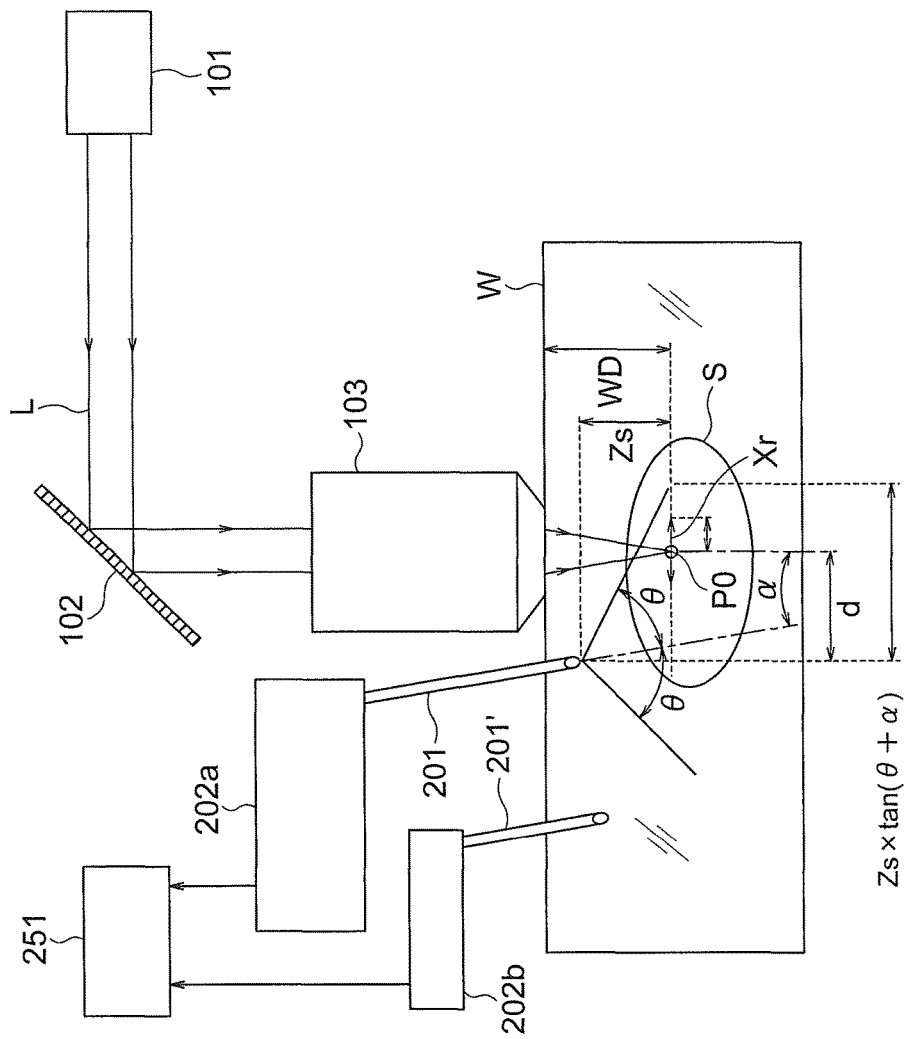

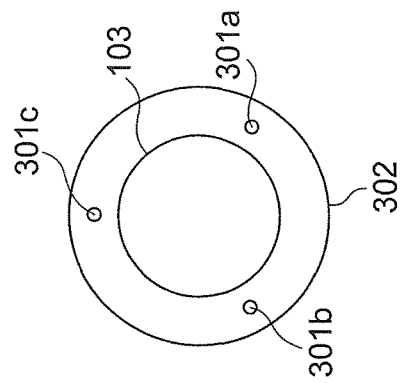
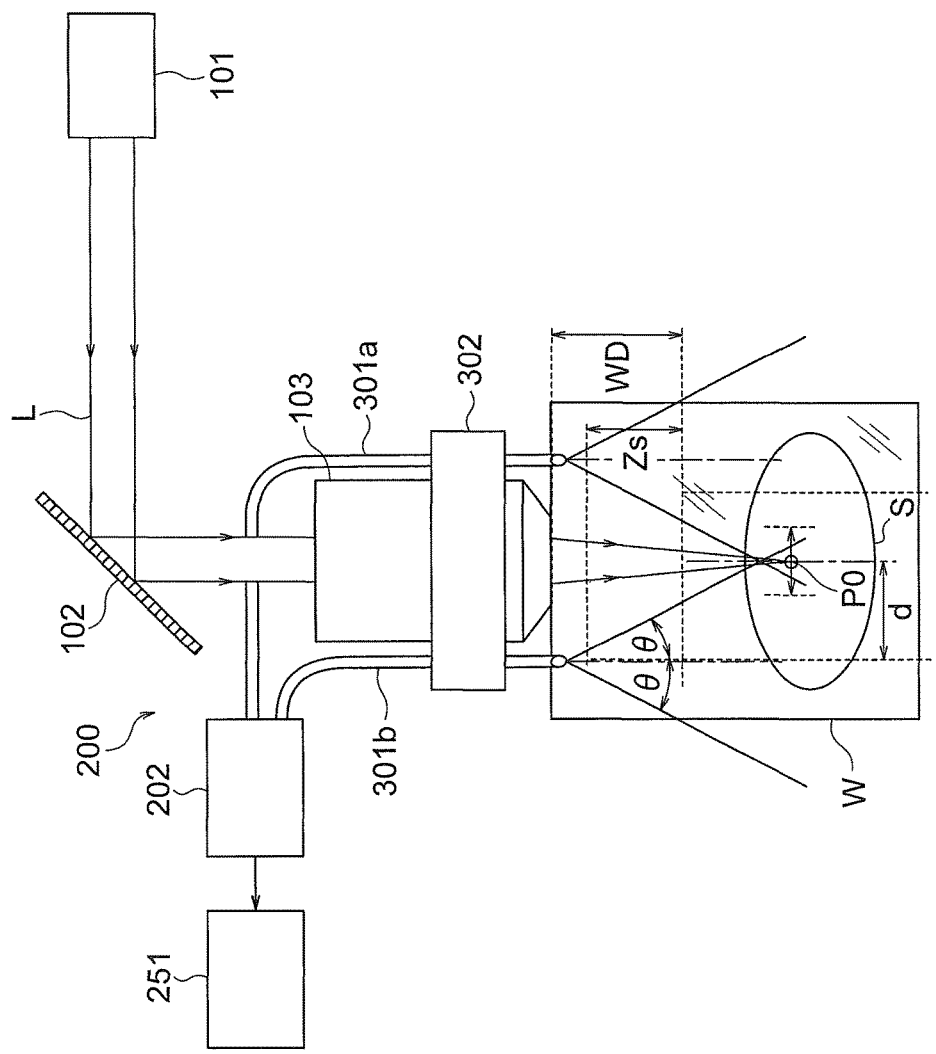
FIG. 8A
FIG. 8B

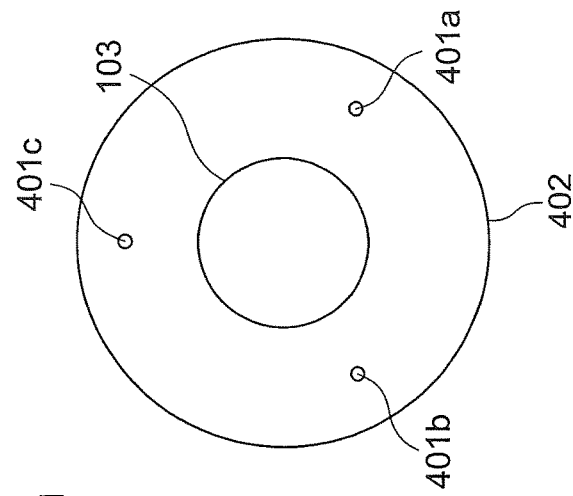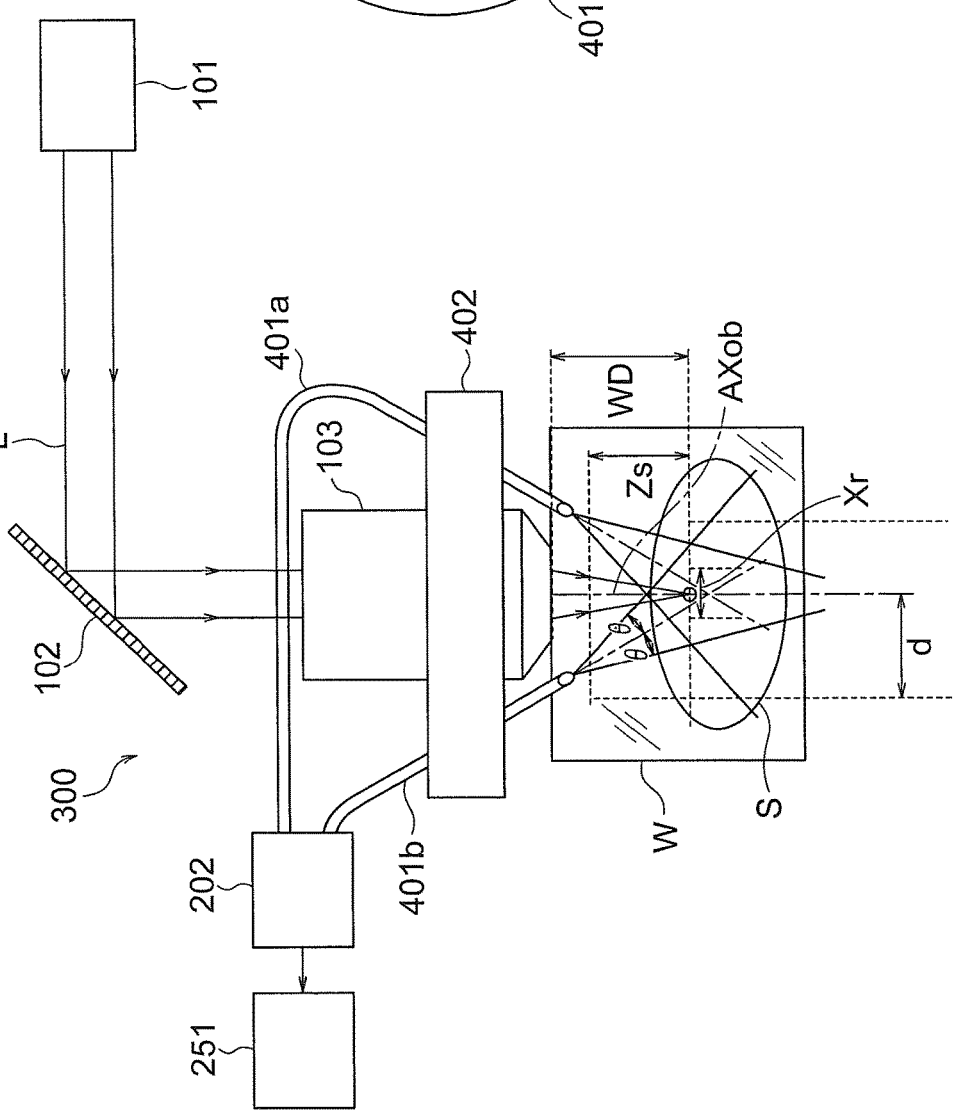

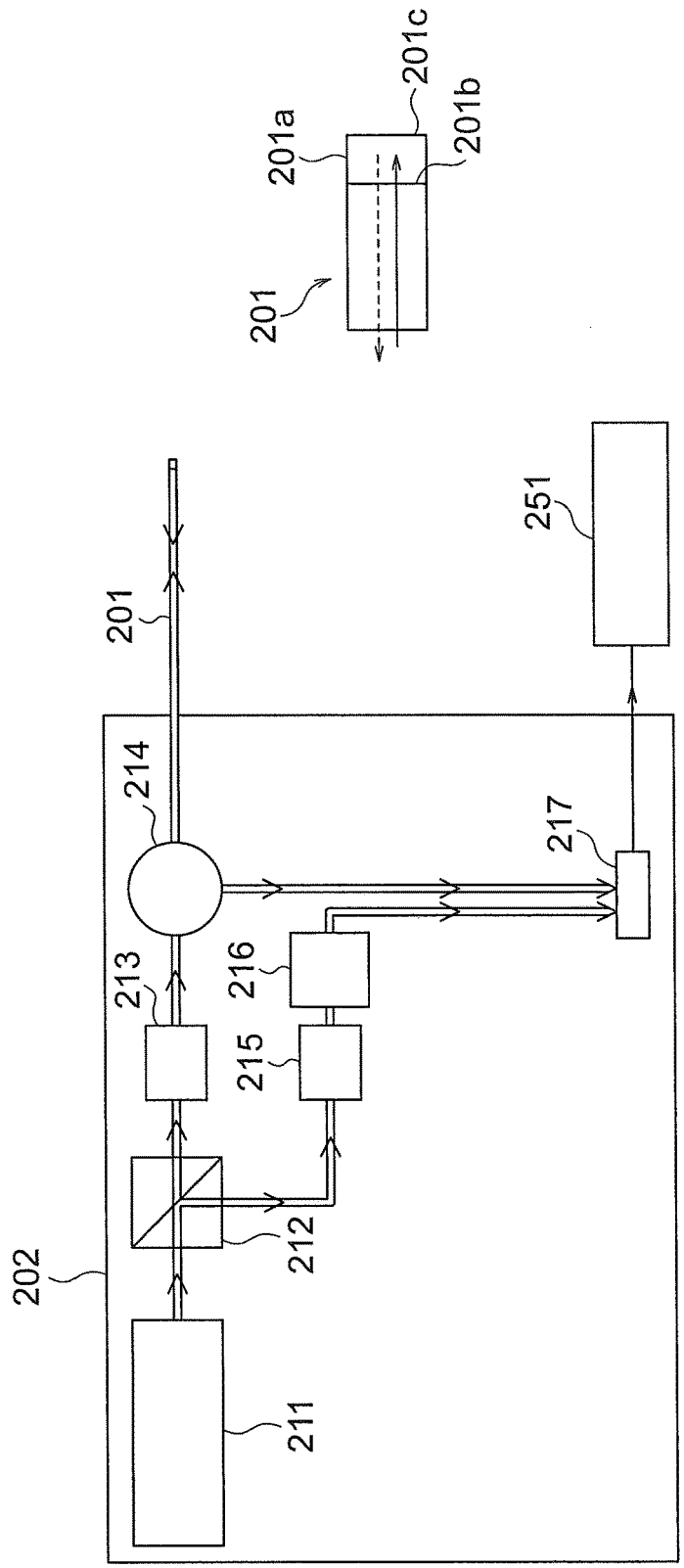

PHOTOACOUSTIC MICROSCOPE APPARATUS

CROSS-REFERENCE TO RELATED APPLICATION

The present application is a continuation application of PCT/JP2015/050292 filed on Jan. 7, 2015 which is based upon and claims the benefit of priority from Japanese Patent Application No. 2014-035423 filed on Feb. 26, 2014; the entire contents of which are incorporated herein by reference.

BACKGROUND OF THE INVENTION

Field of the Invention

The present invention relates to a photoacoustic microscope apparatus.

Description of the Related Art

Photoacoustic waves are a type of elastic waves that are generated in a thermoelastic process which occurs when light of an absorption wavelength range is irradiated to a substance. Therefore, the photoacoustic waves have been attracting attention as a technology for imaging absorption characteristics. Moreover, since the photoacoustic waves are a type of ultrasonic sound waves having characteristics that are not susceptible to be affected by scattering as compared to light, they have been used as a means for imaging inside of an organism.

In an photoacoustic microscope to be used for imaging the photoacoustic wave as a detection signal, a method in which, by using pulse light adapted to the absorption wavelength range of an object to be observed as excitation light, an inside of a specimen is scanned by a focused spot by focusing the excitation light by an objective lens, and the photoacoustic wave generated at positions of the focused spots are detected by a device such as a transducer, has been used. According to the photoacoustic microscope, when the specimen is scanned by the focused spot, since the photoacoustic waves are generated if there is an absorbing substance at the position of the focused spot, it is possible to carry out imaging of absorption characteristics in the specimen by detecting the photoacoustic wave.

As a photoacoustic microscope of such type, a photoacoustic microscope disclosed in Japanese Translation of PCT International Application Publication No. 2011-519281 has been known. FIG. 12 is a diagram showing the photoacoustic microscope disclosed in Japanese Translation of PCT International Application Publication No. 2011-519281. In FIG. 12, excitation light L from a laser pulse light source is focused to an inside of a specimen via a condenser lens 11, a pinhole 12, a vibrating mirror 13, an objective lens 14, a correcting lens 15, an isosceles prism 16, a silicone oil layer 17, a rhombic prism 18, and a photoacoustic lens 19. Moreover, photoacoustic wave U generated from focused positions inside a specimen S are gathered by the photoacoustic lens 19 and are subjected to wave-front conversion, and upon being reflected inside the rhombic prism 18, are detected by an ultrasonic transducer 20.

In FIG. 12, the isosceles prism 16 and the rhombic prism 18 are coupled via the silicone oil layer 17. The photoacoustic lens 19 is cemented to the rhombic prism 18 such that, a sound axis of the photoacoustic lens 19, which corresponds to an optical axis of an optical lens, coincides with an optical axis of the objective lens 14, and a focal position of the photoacoustic lens 19 coincides with a focal position of the objective lens 14. The ultrasonic transducer 20 is joined to the rhombic prism 18 such that, a wave-front of the photoacoustic wave U from a focal point of the photoacoustic lens 19 is converted to a plane wave by the photoacoustic lens 19, and is incident perpendicularly on a detection surface of the ultrasonic transducer 20. Moreover, the specimen S is immersed in a liquid.

SUMMARY OF THE INVENTION

A photoacoustic microscope apparatus according to the present invention includes
a light source that emits excitation light which generates photoacoustic waves,
an objective lens which focuses the excitation light on a specimen,
a scanning unit which moves a focused position of the excitation light on the specimen,
a photoacoustic-wave detecting unit which has a sensor unit that detects a photoacoustic wave generated, and
an image constructing unit which constructs an image based on data from the photoacoustic-wave detecting unit, wherein
the scanning unit includes a movable mirror which changes an angle of incidence of the excitation light incident on the objective lens, and
for the sensor unit, an angle of a range which is capable of receiving the photoacoustic wave incident on the sensor unit is larger than an angle corresponding to a numerical aperture on a side illuminated of the objective lens.

A numerical aperture NA is indicated as NA=1.333×sin (Y).

Here, 1.333 is a refractive index of water, and Y is the maximum angle made by a light beam in a medium (water) between the objective lens and the specimen with an optical axis. The angle corresponding to the numerical aperture refers to the angle Y.

Moreover, an angle θ of the range which is capable of receiving the photoacoustic wave incident on the sensor unit refers to an angle made by a direction of incidence for which, the sensitivity of detecting the photoacoustic signal is the highest with a direction of incidence for which, the sensitivity of detecting the photoacoustic signal is half of the highest sensitivity of detecting.

BRIEF DESCRIPTION OF THE DRAWINGS

FIG. 6 is a diagram showing a photoacoustic microscope apparatus according to a modified example of the first embodiment;

FIG. 8A is a diagram showing a photoacoustic microscope apparatus according to a second embodiment of the present invention, and FIG. 8B is a diagram describing a detector holding unit;

FIG. 9A is a diagram showing a photoacoustic microscope apparatus according to a third embodiment of the present invention, and FIG. 9B is a diagram describing a detector holding unit;

FIG. 10A is a diagram showing a schematic arrangement of a photoacoustic detecting unit, and FIG. 10B is a diagram showing an arrangement of a front end of a fiber sensor;

DETAILED DESCRIPTION OF THE INVENTION

An arrangement of a photoacoustic microscope according to embodiments, and an action and an effect thereof will be described below. However, the present intention is not construed to be limited to the embodiments described below. In other words, description of the embodiments includes number of specific details for exemplification, and variations and modifications made in these details also fall within the scope of the present invention. Therefore, illustrative embodiments of the present invention to be described below are mentioned without loss of generality and without limiting the invention claimed.

(First Embodiment)

Figure 1:
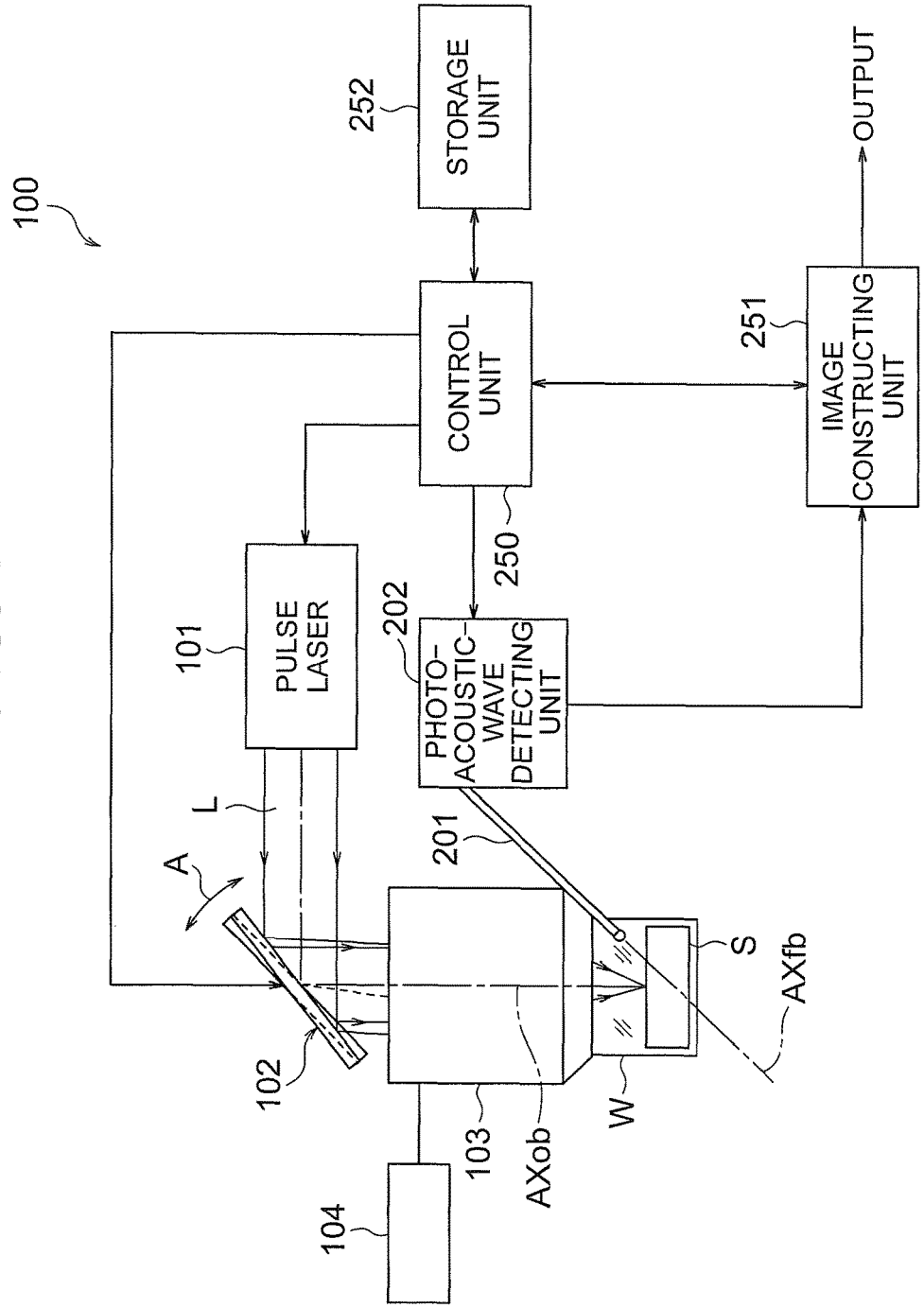
FIG. 1 is a diagram showing a photoacoustic microscope apparatus according to a first embodiment of the present invention.

An arrangement of a first embodiment of the present invention will be described below. As shown in FIG. 1, a photoacoustic microscope apparatus 100 according to the present embodiment includes a pulse light source, for example, a pulse laser 101 that emits excitation light which generates photoacoustic waves, an objective lens 103 which focuses the excitation light on a specimen S, a galvanometer mirror 102 which is a scanning unit that moves a focused position of the excitation light on a specimen, a photoacoustic-wave detecting unit 202 having a sensor unit, for example fiber sensor 201 which detects the photoacoustic waves generated, and an image constructing unit 251 which constructs an image based on data from the photoacoustic-wave detecting unit 202. The fiber sensor 201 has a peculiarity that an angle of a range which is capable of receiving the photoacoustic wave incident on the sensor unit is larger than an angle corresponding to a numerical aperture on a side illuminated of the objective lens.

The objective lens 103 is an immersion lens in which, a space between a front end of the objective lens 103 and the specimen S is filled with a liquid such as a water W.

By such arrangement, a light beam from the pulse laser 101 which is a pulse light source is reflected by the galvanometer mirror. Moreover, the light beam is incident at a predetermined angle on the objective lens 103 for focusing excitation light L on the specimen S.

The light beam incident on the objective lens 103 is focused in the specimen S via the water W. At a position inside the specimen S where the light is focused, if there is a substance which generates photoacoustic waves, the photoacoustic waves are generated inside the specimen S.

Next, an arrangement for scanning the specimen S by the excitation light L will be described below.

A photoacoustic wave signal (photoacoustic signal) is propagated through the specimen S, and further through the water W. A photoacoustic wave Lr propagated through the water W reaches a fiber sensor 201 included in the photoacoustic detecting unit 202.

Figure 2A:
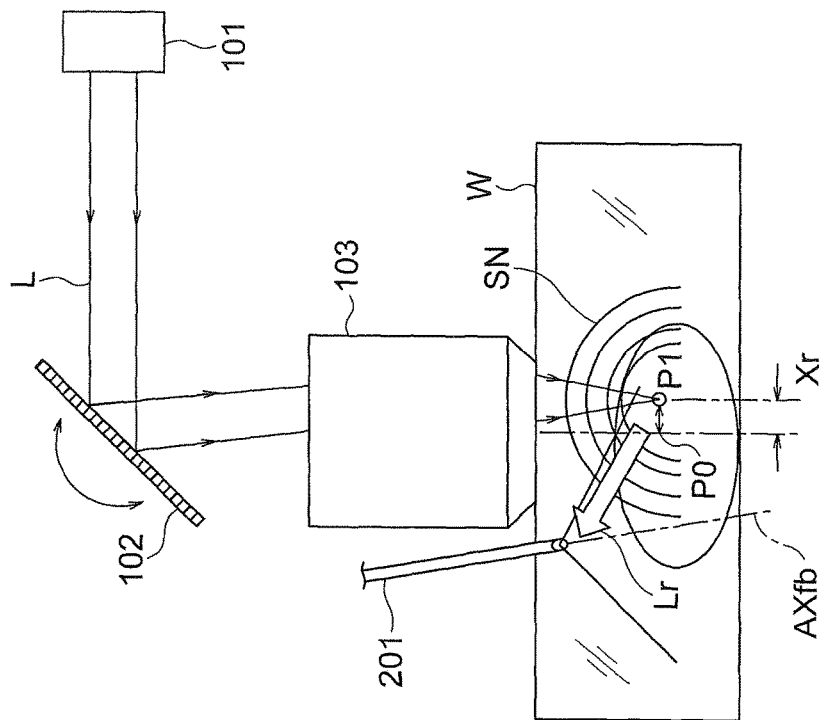
FIG. 2A and FIG. 2B are diagrams showing a state when a galvanometer mirror 102 is vibrated.
Figure 2B:
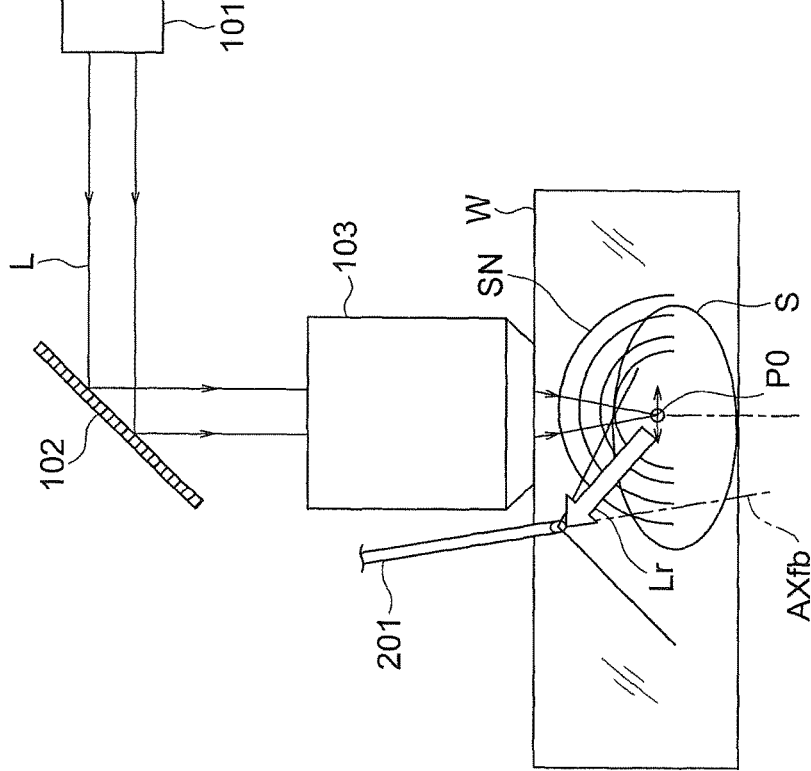

FIG. 2A and FIG. 2B show a state when the galvanometer mirror is vibrated.

In FIG. 2A, an optical path of the excitation light L from the pulse laser 101 is bent by 90 degrees by the galvanometer mirror 102. Moreover, the excitation light L which is parallel is incident almost perpendicularly on the objective lens 103. The objective lens 103 focuses the incident excitation light L at a focal position.

A photoacoustic wave SN is generated at a focused-spot position P0 inside the specimen S. The photoacoustic wave SN advances while propagating through the specimen S, and further through the inside of the water W. The photoacoustic wave Lr which is a part of the photoacoustic wave SN propagated through the water W reaches a front-end portion of the fiber sensor 201.

FIG. 2B shows a state in which, the galvanometer mirror 102 is made to vibrate (tilt) in a direction of an arrow on a paper surface as compared to a state shown in FIG. 2A. As the galvanometer mirror is made to vibrate, an optical path of the excitation light L from the pulse laser 101 for instance, is bent by a predetermined angle while being parallel light as it has been, by the galvanometer mirror 102. Further, the parallel excitation light L is incident obliquely on the objective lens 103. The objective lens 103 focuses the excitation light L incident obliquely, at a focused-spot position P1.

Here, the focused-spot position P1 (FIG. 2B) is a position different from the focused-spot position P0 (FIG. 2A). In such manner, two-dimensional scanning of the inside of the specimen S along a first scanning direction and a second scanning direction by the focused spots of the excitation light L is possible by the galvanometer mirror 102.

The area of the specimen S that can be scanned by the excitation light L is let to be a radius Xr of a scanning range (in other words, radius of the maximum area to be observed).

Furthermore, by changing a relative distance between the objective lens 103 and the specimen S, it is possible to move a position of the focused spot in a direction of depth of the specimen S. Moreover, as aforementioned, the objective lens 103 of different focal length may be selected appropriately, and mounted.

In a case in which, the photoacoustic wave SN is generated at the focused-spot position P1 inside the specimen S, the photoacoustic wave SN advances through the inside of the specimen S, and further through the inside of the water W. The photoacoustic wave Lr which is a part of the photoacoustic wave SN propagated through the water W reaches the front-end portion of the fiber sensor 201 of the photoacoustic-wave generating unit 202. The photoacoustic-wave detecting unit 202 is an interferometer which computes the photoacoustic wave Lr that was detected. An arrangement in detail of the photoacoustic-wave detecting unit 202 will be described later.

Moreover, an image constructing unit 251 is connected to a control unit 250. The control unit 250 compiles a database of a correspondence relationship of an output signal and an irradiation position of the excitation light, based on an output signal obtained from the photoacoustic-wave detecting unit 202, in synchronization with a drive of the galvanometer mirror 102 by the control unit 250, or in other words, in synchronization with an irradiation timing of the excitation light L at the time of two-dimensional scanning inside a plane of the specimen S. For example, when the control unit 250 associates the irradiation position of the excitation light L and a signal strength of a signal obtained, the irradiation position of the excitation light and an output waveform that was obtained may be associated.

Moreover, in a case of imaging data of a scanned surface of the specimen S, the imaging is carried out by the image constructing unit 251. Data subjected to imaging is stored in a storage unit 252 and is displayed on a monitor which is not shown in the diagram. The image constructing unit 251 may have been built-in in the control unit 250.

Figure 3:
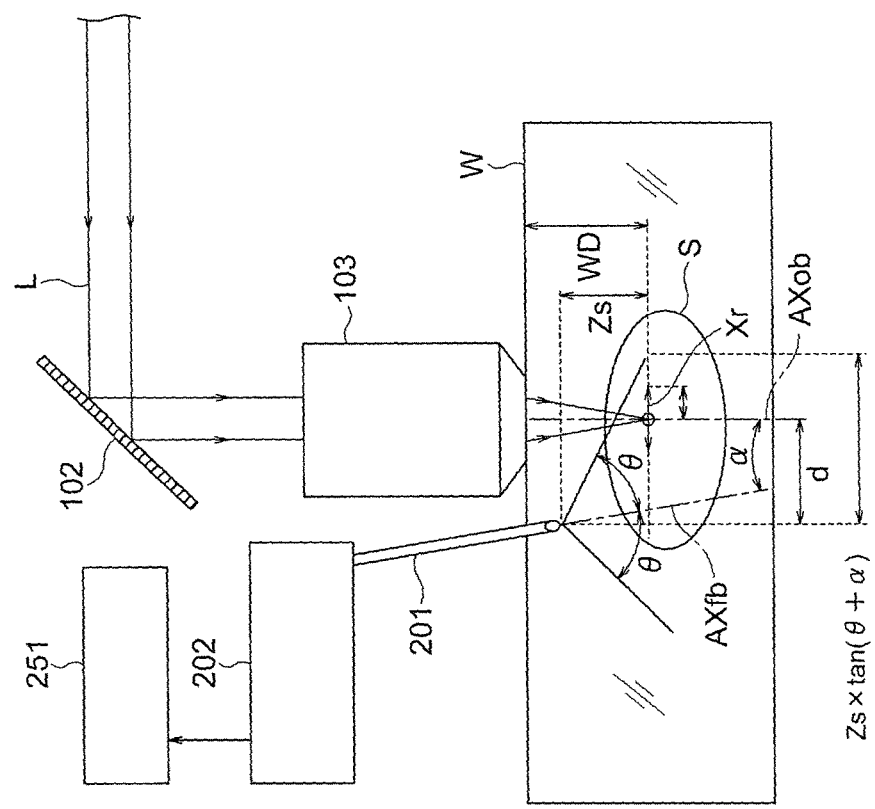
FIG. 3 is a diagram explaining parameters.

Moreover, in the present embodiment, it is desirable that the photoacoustic microscope apparatus satisfies the following conditional expression (1).

$$Zs \times \tan(\theta+\alpha) > Xr + d \qquad (1)$$

where, as shown in FIG. 3

NA denotes a numerical aperture of the objective lens 103 (for high magnification), φ (mm) denotes an actual field of view (two times of Xr), Xr (mm) denotes a radius of the maximum area to be observed, WD (mm) denotes a working distance of the objective lens 103, Zs (mm) denotes a distance between the front-end portion of the fiber sensor 201 and a focused position of the objective lens 103, θ (degree) denotes a range of an angle of a light beam that can be incident on the front-end portion of the fiber sensor 201, d (mm) denotes a distance in an observation plane (in an xy plane) perpendicular to an optical axis AXob, between the optical axis AXob of the objective lens 103 and the fiber sensor 201, and α (degree) denotes an angle made by a central axis AXfb of the fiber sensor 201 and the optical axis AXob of the objective lens 103.

In the present embodiment, by making an arrangement to satisfy conditional expression (1), it is possible to secure an area in which, sensitivity of detection is high.

Corresponding values of conditional expression (1) in the present embodiment are shown below.

| | |
|---|---|
| NA | 0.75 |
| φ (mm) | 1 |
| WD (mm) | 11 |
| Zs (mm) | 10 |
| θ (degree) | 45 |
| d (mm) | 15 |
| α (degree) | 30 |
| Xr (mm) | 0.5 |
| Zs × tan (θ + α) | 37.32 |
| Xr + d | 15.5 |

Moreover, it is desirable that the distance Zs in the direction along the optical axis of the objective lens, between the focused position of the objective lens 103 and the fiber sensor 201 is shorter than a distance from the front-end portion of the objective lens 103 up to the focused position, or in other words, the working distance WD.

In the present embodiment, as aforementioned, Zs=10 and WD=11. In such manner, it is possible to secure a sufficient working distance.

Figure 4A:
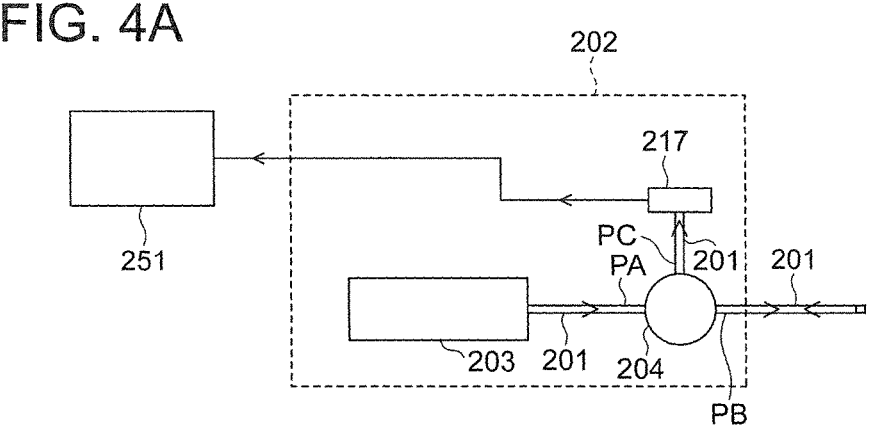
FIG. 4A is a diagram showing an arrangement of a photoacoustic-wave detecting unit.

FIG. 4A shows an arrangement of the photoacoustic-wave detecting unit 202. A laser diode 203 emits light of a wavelength λ=1000 nm. The light from the laser diode 203 is incident from a port PA of an optical circulator 204, and upon advancing and passing through, emerges from a port PB. Light emerged from the port P is input to one of terminals of the fiber sensor 201.

Figure 4B:
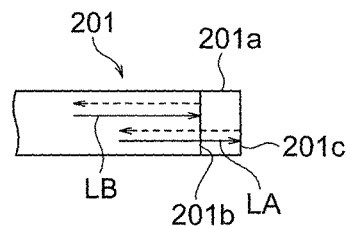
FIG. 4B is a diagram showing an arrangement of an end portion of a fiber sensor.

FIG. 4B shows an arrangement of an end-portion of the fiber sensor 201. A thin film 201a is formed at the end portion of the fiber sensor 201. The thin film 201a has a reference surface 201b for a photoacoustic wave for reference and an object-side surface 201c on a specimen side.

Description will be made coming back to FIG. 4A.

Of a light beam emerged from the port PB of the optical circulator 204, the photoacoustic signal (wave) Lr that is irradiated to the specimen S as aforementioned, and returned once again is to be taken into consideration. The photoacoustic signal (wave) Lr is incident on the port PB of the optical circulator 204. The photoacoustic signal (wave) Lr incident on the port PB emerges from a port PC this time.

A silicon photodetector 217 receives light from the port PC. In the silicon photodetector 217, an intensity signal in which, two light beams have interfered is achieved.

As it has been explained by using FIG. 4B, the thin film 201a is formed at the end portion on the specimen S side of the fiber sensor 201. A front end of the fiber sensor 201 is immersed in the water W. A light beam reflected at the reference surface 201b of the thin film 201a returns toward the optical circulator 204 as a reference light.

As the photoacoustic signal (wave) Lr from the specimen S reaches the front end of the fiber sensor 201, a film thickness of the thin film 201a changes. A light beam reflected at the reference surface 201b and a light beam reflected at an object-side surface 201c, return with the same optical path, and reach the optical circulator 204.

Consequently, an intensity of light changes due to interference, and a photoacoustic signal is acquired as an intensity signal of light.

A photoacoustic intensity signal (light beam) that was incident from the port PB of the optical circulator 204 is thereafter incident on the silicon photodetector 217. The image constructing unit 251 constructs an image based on intensity information of light by interference. A procedure for image construction will be described later.

Figure 4C:
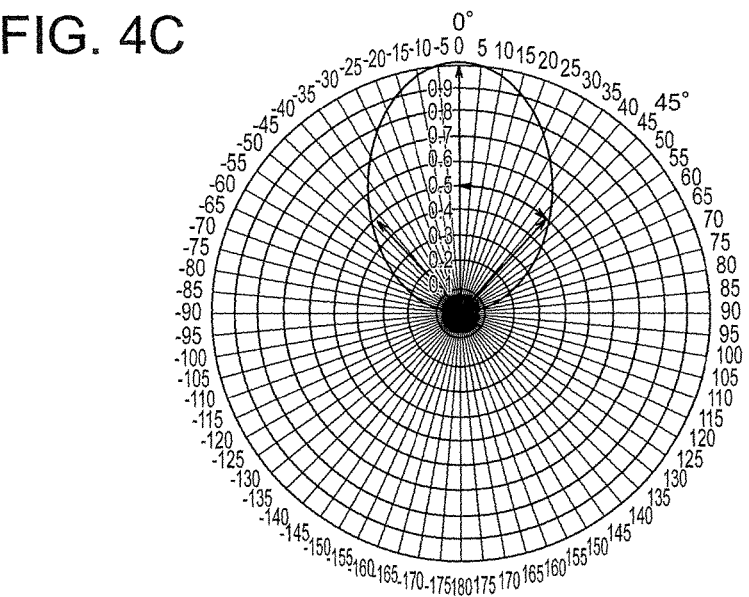
FIG. 4C is a diagram showing a distribution of directionality of the fiber sensor.

FIG. 4C shows a relationship of an angle and sensitivity for the fiber sensor 201. Regarding the angle, an angle at which, a light beam incident along the central axis AXfb (for example, refer to FIG. 2A and FIG. 2B) of the directionality of the fiber sensor 201, is let to be 0 degrees. Moreover, the sensitivity is indicated upon normalizing, letting the maximum sensitivity to be 1.

For instance, the sensitivity of detecting a photoacoustic signal incident from a direction of 45 degrees with respect to the central axis AXfb is about ½ (signal strength=0.5) with respect to the sensitivity of detecting a signal (signal strength=1) that is incident axially from the central axis AXfb.

Figure 5A:
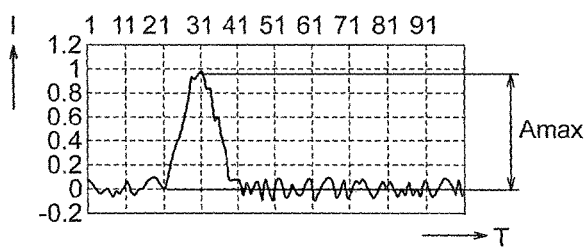
FIG. 5A is a diagram showing a photoacoustic wave signal.

FIG. 5A shows a photoacoustic wave signal obtained by the photoacoustic-wave detecting unit 202. A horizontal axis in FIG. 5A indicates time T, and a vertical axis in FIG. 5A indicates signal strength I. In such manner, the photoacoustic wave signal is a time-series signal.

The maximum value Amax of an amplitude of the signal is let to be of a magnitude of a photoacoustic wave signal from a focal point. Moreover, position information of a focal point of the objective lens 103 is acquired from a deflection angle of the galvanometer mirror 102.

Figure 5B:
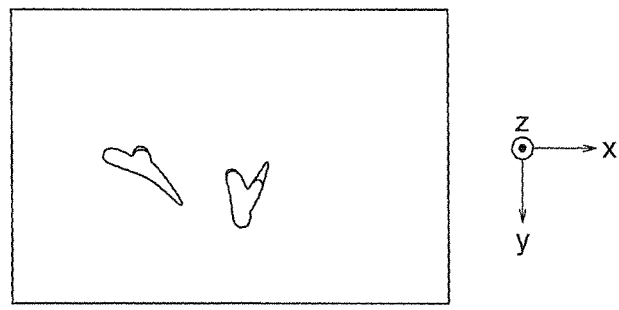
FIG. 5B is a diagram showing a two-dimensional mapping.
Figure 5C:
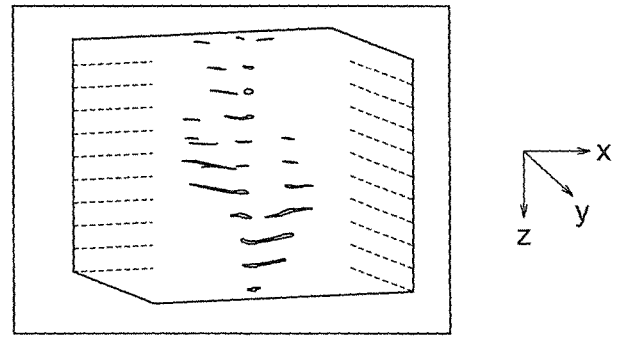
FIG. 5C is a diagram showing information of a direction of depth of a specimen.

Consequently, the image constructing unit 251 is capable of carrying out two-dimensional mapping as shown in FIG. 5B by the position information and the magnitude of the photoacoustic signal. FIG. 5B shows a result of imaging upon carrying out mapping of specific intensity of inside of the specimen S according to an xy position of scanning.

Furthermore, an objective-lens drive unit 104 (FIG. 1) moves the objective lens 103 in a direction z along the optical axis AXob. As a result, it is possible to acquire information of the specimen S in direction z of depth.

The image constructing unit 251 computes the objective lens 103 based on the information in the direction z of depth. Moreover, the image constructing unit 251 carries out the abovementioned photoacoustic-wave detection of the inside of the specimen S.

Figure 5D:
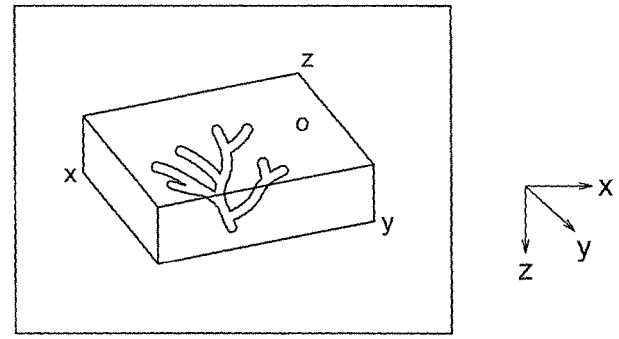
FIG. 5D is a diagram showing a three-dimensional photoacoustic wave image.

As shown in FIG. 5D, the image constructing unit 251 changes a position of the objective lens 103, and once again acquires an image. Accordingly, it is possible to achieve a plurality of images in the direction z. Accordingly, a three-dimensional photoacoustic-wave image of the sample S is constructed.

As aforementioned, a range in which, detection of a position at which the sensitivity is 50% corresponding to a state of the optimum sensitivity (angle in FIG. 4C is 0 degrees) is possible is let to be the range of directionality in which, the fiber sensor 201 is capable of detecting and acquiring the photoacoustic wave signal.

As described above, in the present embodiment, a conventional prism and an acoustic lens are unnecessary. Accordingly, since it is possible to secure a substantial distance (WD) up to the specimen S, it is possible to observe brightly, and to observe deeper portion of the specimen S.

Moreover, since an acoustic lens is unnecessary for the excitation light L, an observation with a satisfactory optical performance (numerical aperture) of the objective lens 103 is possible. Furthermore, by the fiber sensor 201 with a wide directionality, it is possible to widen a range in which, the specimen S can be observed.

Figure 12:
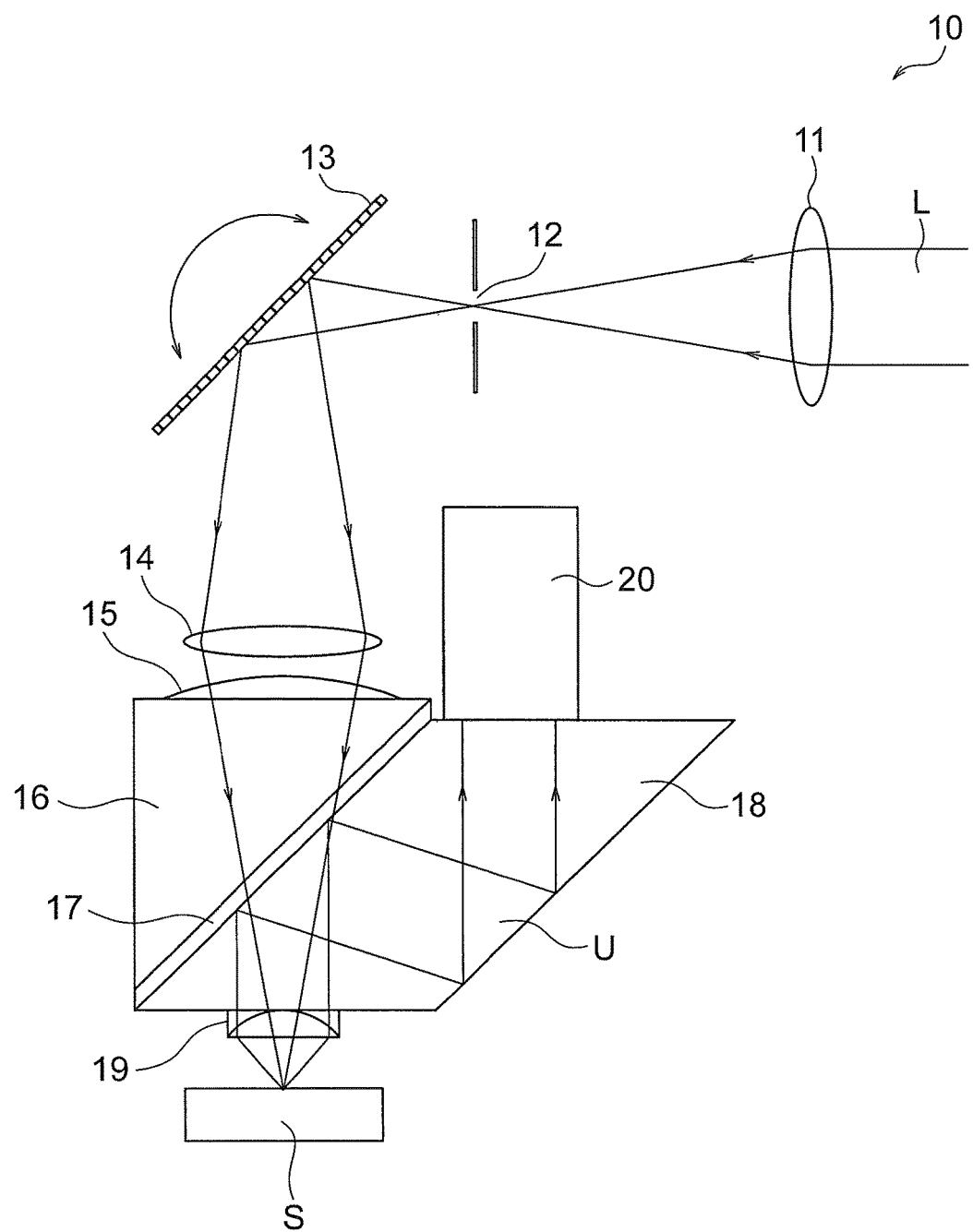
FIG. 12 is a diagram describing an arrangement of a conventional photoacoustic microscope.

Moreover, in an arrangement in a prior art in FIG. 12, in order that a photoacoustic wave U from a specimen S is incident perpendicularly all the time on an ultrasonic transducer 20, instead of the scanning by a vibrating mirror 13, moving an incidence system for excitation light L including an objective lens 14, a detection system for the photoacoustic wave U including a photoacoustic lens 19, and a specimen stage on which a specimen S is to be mounted, in a relative manner is to be envisioned. However, in this case, it takes a long time for scanning.

Whereas, in the present embodiment, at the time of scanning, the movement of the objective lens and the specimen stage is unnecessary. Consequently, an effect that a high-speed scanning is possible is shown.

(Modified Example of First Embodiment)

FIG. 6 shows an arrangement of a photoacoustic microscope apparatus according to a modified example of the first embodiment. As shown in FIG. 6, the arrangement is such that, the photoacoustic wave signal is detected from a position different from the focal (focused spot) position P0 of the objective lens 103. The control unit and the storage unit are omitted in the diagram.

In the present modified example, the photoacoustic microscope apparatus includes a separate new fiber sensor 201' and a photoacoustic-wave detecting unit 202b.

Figure 7A:
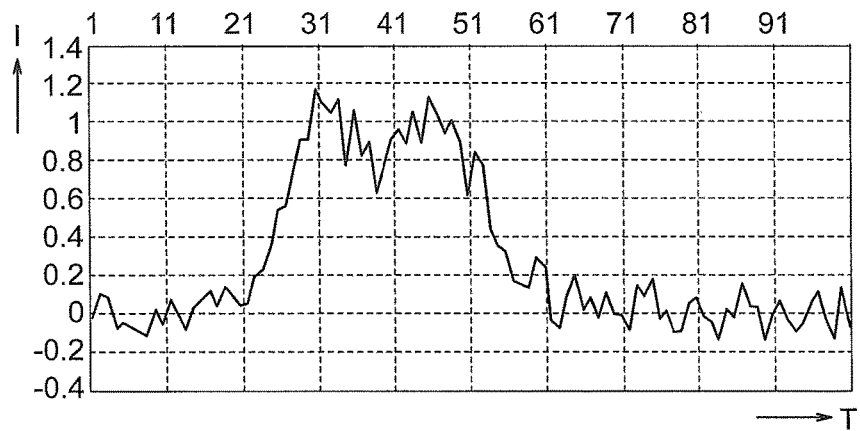
FIG. 7A is a diagram showing a photoacoustic wave signal detected by a fiber sensor.

FIG. 7A shows a photoacoustic wave signal detected by the fiber sensor 201.

For instance, for the photoacoustic wave signal from the sample S detected only by the fiber sensor 201, since the thin film at the front end of the fiber sensor 201 observes a displacement of the water W, not only the photoacoustic wave Lr from the sample S but also external vibrations due to air turbulence, and external vibrations due to a movement of the specimen S affect the photoacoustic wave signal from the sample S.

Figure 7B:
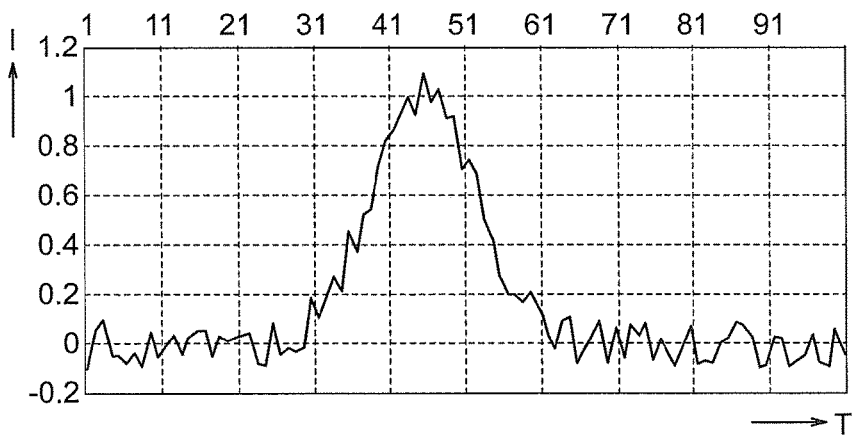
FIG. 7B is a diagram showing a photoacoustic wave signal detected by another fiber sensor.

FIG. 7B shows a photoacoustic wave signal detected by the fiber sensor 201'. The fiber sensor 201' detects a signal from an area other than the sample S.

Figure 7C:
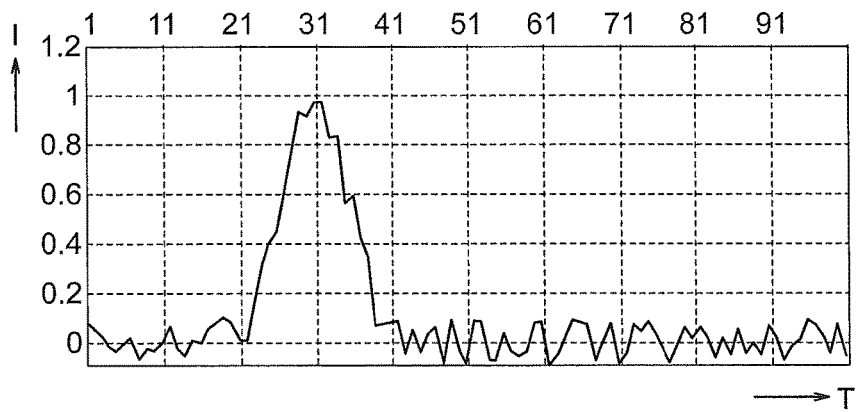
FIG. 7C is a diagram showing a photoacoustic wave signal detected by still another fiber sensor.

Therefore, a difference between an intensity distribution of the photoacoustic wave signal shown in FIG. 7A and an intensity distribution of the photoacoustic wave signal shown in FIG. 7B is taken. The result thereof is shown in FIG. 7C. In the present example, it becomes possible to detect only the signal from the specimen S. Consequently, a highly accurate detection in which, noise due to external factors is eliminated, or in other words, an effect of an external environment is reduced, becomes possible.

Optimally, it is necessary that fiber sensor 201' acquires a photoacoustic signal from a portion other than the specimen S. For this, it is desirable to dispose such that a direction with the highest directionality is directed in a direction opposite to the specimen S.

(Second Embodiment)

Next, a photoacoustic microscope apparatus according to a second embodiment of the present invention will be described below by referring to FIG. 8A.

Same reference numerals are assigned to components which are same as in the first embodiment, and repetitive description of such components is omitted. Moreover, the control unit and the storage unit are omitted.

A fiber sensor (sensor unit) of the photoacoustic-wave detecting unit 202 includes a plurality of sensor groups, for example, three fiber sensors 301a, 301b, and 301c.

It is desirable that the plurality of fiber sensors 301a, 301b, and 301c is capable of making the photoacoustic wave Lr from a range of the specimen S that can be scanned by the galvanometer mirror 102 which is a scanning unit, incident on an arbitrary range from a desired range up to the entire range.

Accordingly, it is possible to observe the photoacoustic wave from the range of the specimen in the arbitrary range from the desired range up to the entire range, over a wide range.

Furthermore, it is desirable that the image constructing unit 251 is capable of detecting a position of a signal generating source in the specimen S based on information (photoacoustic wave signal) from the plurality of sensor groups (fiber sensors) 301a, 301b, and 301c.

Accordingly, it is possible to detect the position of the signal generating source more accurately based on the plurality of information (photoacoustic wave signals).

Moreover, in the present embodiment, it is desirable that the photoacoustic microscope apparatus 200 further includes a detector holding unit 302 for holding the sensor groups 301a, 301b, and 301c in the sensor unit, in a peripheral portion of the objective lens 103.

FIG. 8B shows an arrangement of the detector holding unit 302 as viewed from an optical axial direction of the objective lens 103.

Accordingly, with a simple arrangement, a degree of freedom of disposing the sensor groups is improved. As a result, it is possible to widen the working distance as well as to widen an observation area in the xy plane.

In the present embodiment, the three fiber sensors 301a, 301b, and 301c for detecting the photoacoustic signal are provided discretely at an interval of 120 degrees in the circular cylinder shaped detector holding unit 302.

Accordingly, even in a case in which, the range to be observed by scanning cannot be covered sufficiently in one fiber sensor, it is possible to create an image of the photoacoustic wave signal by combining information from the plurality of fiber sensors.

The image constructing unit 251 constructs an image based on information of focused positions of the objective lens 103 by the galvanometer mirror 102 and information detected from one of the corresponding fiber sensors 301a, 301b, and 301c.

Moreover, in a case in which, the detection range of a fiber sensor from among the three fiber sensors is outside the range of the photoacoustic wave signal, it is possible to use that fiber sensor as a sensor which eliminates noise as described in the abovementioned modified example.

Corresponding values of conditional expression (1) in the present embodiment are shown below.

| | |
|---|---|
| NA | 0.15 |
| φ (mm) | 5 |
| WD (mm) | 20 |
| Zs (mm) | 18 |
| θ (degree) | 30 |
| d (mm) | 15 |
| α (degree) | 0 |
| Xr (mm) | 2.5 |
| Zs × tan (θ + α) | 10.39 |
| Xr + d | 17.5 |

(Third Embodiment)

Next, a photoacoustic microscope apparatus according to a third embodiment of the present invention will be described below.

FIG. 9A shows an arrangement of the present embodiment. Same reference numerals are assigned to components which are same as in the first embodiment and the second embodiment, and repetitive description of such components is omitted. Moreover, the control unit and the storage unit are omitted.

In the present embodiment, as compared to the second embodiment, an arrangement is made such that, it is possible to detect a signal from an area that can be observed by scanning even by one fiber sensor from among a plurality of fiber sensors 401a, 401b, and 401c.

Concretely, for instance, the three fiber sensor groups 401a, 401b, and 401c are to be used. FIG. 9B shows an arrangement when the detector holding unit 302 is viewed from the optical axial direction of the objective lens 103.

An arrangement is made such that, it is possible to detect the position information of the focused spot of the objective lens 103 and the photoacoustic wave signal more accurately, based on plurality of signals from the fiber sensor groups 401a, 401b, and 401c.

Furthermore, in the present embodiment, the photoacoustic-wave detecting unit 202 observes an amount of change in the thin film 201a of the fiber sensor 201 by heterodyne interferometry shown in FIG. 10A and FIG. 10B.

FIG. 10A shows a schematic arrangement of the photoacoustic-wave detecting unit 202. In the heterodyne interferometry, it is necessary to modulate light (of wavelength λ=1000 nm for example) from a laser diode 211 at a specific frequency.

A beam splitter 212 divides the light from the laser diode 211 into object light that is transmitted and reference light that is reflected. Moreover, a frequency shifter for reference 215 and a frequency shifter for observation 216 are to be used.

Moreover, a light beam transmitted through the beam splitter 212 passes through the frequency shifter for observation 213, and an optical circulator 214. Thereafter, the light beam is incident on the fiber sensor 201.

As shown in FIG. 10B, the fiber sensor 201 has the thin film 201a formed on the specimen S side. Here, a reflectance of the object-side surface 201c on the specimen S side is higher than a reflectance of the object-side surface 201c on an opposite side of the specimen S.

As a result, light from the specimen S side is reflected and passes through the fiber sensor 201. Moreover, due to the optical circulator 214, the photoacoustic wave signal from the specimen S is incident on the silicon photodetector 217.

On the other hand, a light beam transmitted through the frequency shifter for reference 215 is incident on the silicon photodetector 217 via an optical path for reference having an optical path length substantially same as a round-trip optical path length of a fiber. An amount of light that is detected by the silicon photodetector 217 becomes a resonance signal corresponding to two light frequencies, one for reference and one for observation.

The image constructing unit 251 analyses the resonance signal. Accordingly, it is possible to detect a change in a film thickness of an end portion of the fiber sensor 201 with higher accuracy.

Figure 11A:
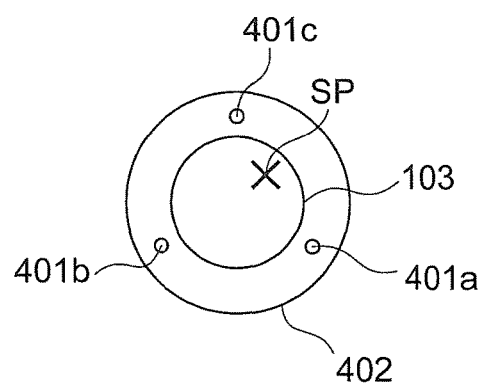
FIG. 11A is a diagram showing an arrangement when the detector holding unit is viewed from an optical axial direction of an objective lens, and each of FIG. 11B, FIG. 11C.

Next, a principle of measuring a focused position in the direction z of depth of the specimen S in the present embodiment will be described below. FIG. 11A shows an arrangement when a detector holding unit 402 is viewed from the optical axial direction of the objective lens 103. Here, for example, three fiber sensor groups 401a, 401b, and 401c are to be used. A cross-mark SP in FIG. 11A indicates a focused position of the objective lens 103 positioned at a certain depth from a surface of the specimen S.

In the present embodiment, a central axis of the three fiber sensor groups 401a, 401b, and 401c and the optical axis AXob of the objective lens 103 make a predetermined angle. From co-ordinates (x, y) of the focused position of the objective lens 103 assigned to the galvanometer mirror 102 and the time taken by the photoacoustic wave signal to reach an observation target inside the specimen S, it is possible to compute the direction z of depth (sound-source position) with respect to the respective fiber sensor position.

Accordingly, in the present embodiment, it is possible to achieve the direction z of depth of the observation target with high accuracy, based on a z-position depth of a sound source acquired from the three fiber sensors 401a, 401b, and 401c.

Figure 11B:
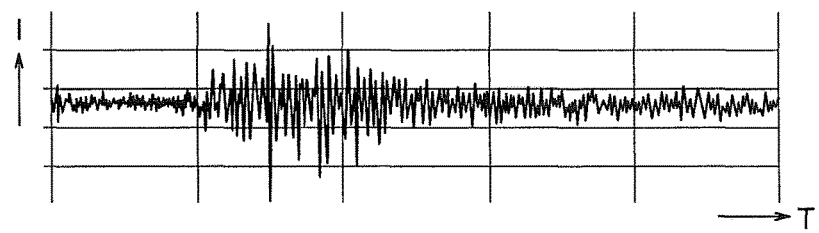
FIG. 11D is a diagram showing a photoacoustic wave signal detected by a different fiber sensor.

FIG. 11B shows a photoacoustic wave signal detected by the fiber sensor 401a.

Figure 11C:
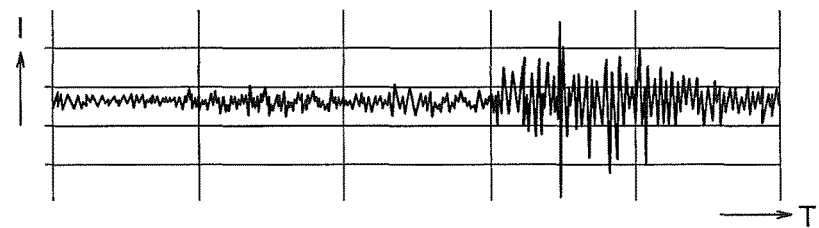
Figure 11D:
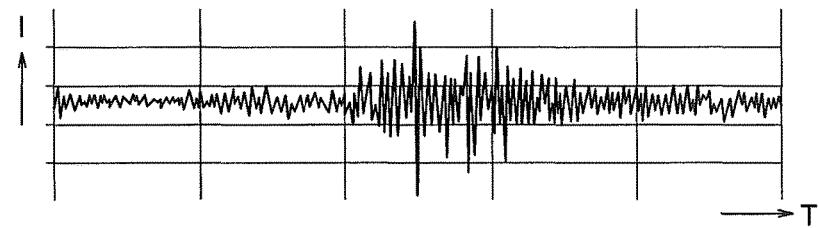

FIG. 11C shows a photoacoustic wave signal detected by the fiber sensor 401b.

FIG. 11C shows a photoacoustic wave signal detected by the fiber sensor 401C.

Corresponding values of conditional expression (1) according to the present embodiment are shown below.

| | |
|---|---|
| NA | 0.5 |
| φ (mm) | 2 |
| WD (mm) | 15 |
| Zs (mm) | 12 |
| θ (degree) | 30 |
| d (mm) | 12 |

-continued

| | |
|---|---|
| α (degree) | 25 |
| Xr (mm) | 1 |
| Zs × tan (θ + α) | 17.14 |
| Xr + d | 13 |

In the pulse laser 101, with an organism as the specimen S, in a case of imaging a blood vessel inside the organism, excitation light L of an absorption wavelength of hemoglobin is irradiated. Without restricting the observation target to the blood vessel, it is also possible to use for imaging of an endogenous substance such as melanin. In this case, light of an absorption wavelength range of a substance which is the target of observation may be used as the excitation light L.

Moreover, it is also possible to use for imaging of an endogenous substance such as a fluorescent body and metallic nanoparticles. In such case of a fluorescent body, light of absorption wavelength region of the fluorescent body which is the target, and in a case of metallic nanoparticles, light of resonance wavelength region of the metallic nanoparticles which is the target, may be used as the excitation light L.

In a case in which there is a plurality of absorbing bodies inside the specimen S, it is desirable to use light of a wavelength of a peak of a characteristic absorption spectrum of the observation target. The timing of emitting the pulse light from the pulse laser 101 is controlled by the control unit 250.

Here, the objective lens 103 of a different wavelength is to be selected appropriately and mounted.

As described heretofore, the present invention can take various modified examples without departing from the scope of the invention. For example, in each of the abovementioned embodiments, the galvanometer mirror is used for making the excitation light vibrate. The arrangement is not restricted to such arrangement, and may be an arrangement which enables to deflect a beam.

The present invention shows an effect that it is possible to provide a photoacoustic microscope apparatus in which, a sufficiently long working distance can be secured, and which is capable of scanning in units of a large area over a wide scanning range and improving the accuracy of detection.

As described heretofore, the photoacoustic microscope apparatus according to the present invention is an apparatus in which, it is possible to secure a sufficiently long working distance, and which is capable of scanning in units of a large area over a wide scanning range, and improving the accuracy of detection.

What is claimed is:

1. A photoacoustic microscope apparatus comprising:
a light source that emits an excitation light which generates photoacoustic waves;
an objective lens which focuses the excitation light on a specimen;
a scanning unit which moves a focused position of the excitation light on the specimen;
a photoacoustic-wave detecting unit which has a fiber sensor that detects the photoacoustic waves generated; and
an image constructing unit which constructs an image based on data from the photoacoustic-wave detecting unit, wherein
the scanning unit includes a movable mirror which changes an angle of incidence of the excitation light incident on the objective lens,
for the fiber sensor, an angle of a range which is capable of receiving the photoacoustic waves incident on the fiber sensor is larger than an angle corresponding to a numerical aperture on a side illuminated of the objective lens, and
the photoacoustic microscope apparatus satisfies the following conditional expression:

$$Zs \times \tan(\theta+\alpha) > Xr+d$$

where,
θ denotes an angle of a range in which, the fiber sensor can receive the photoacoustic waves,
α denotes an angle made by a central axis of a directionality of the fiber sensor with an optical axis of the objective lens,
Xr denotes a radius of the maximum area to be observed,
d denotes a distance in an observation plane perpendicular to the optical axis, between the optical axis of the objective lens and the fiber sensor, and
Zs denotes a distance in a direction along the optical axis of the objective lens, between a focused position by the objective lens and the fiber sensor.

2. The photoacoustic microscope apparatus according to claim 1, wherein
the fiber sensor of the photoacoustic-wave detecting unit has a plurality of fiber sensor groups, and
the plurality of fiber sensor groups is capable of making the photoacoustic waves from a range of the specimen that can be scanned by the scanning unit, incident on an arbitrary range from a desired range up to the entire range.

3. The photoacoustic microscope apparatus according to claim 2, wherein the image constructing unit, detects a position of a signal generating source in the specimen based on a photoacoustic wave signal from the plurality of fiber sensor groups.

4. The photoacoustic microscope apparatus according to claim 1, further comprising:
a detector holding unit for holding the fiber sensor, which is disposed in a peripheral portion of the objective lens.

5. The photoacoustic microscope apparatus according to claim 1, wherein the distance in the direction along the optical axis of the objective lens, between the focused position of the objective lens and the fiber sensor is shorter than a distance from a front-end portion of the objective lens up to the focused position.

6. The photoacoustic microscope apparatus according to claim 1, wherein
the fiber sensor includes a fiber, and
the fiber has an interference film which is provided directly to a front end of the fiber, and
the interference film has a reference surface for the photoacoustic waves for reference, and an object-side surface on a specimen side.

7. The photoacoustic microscope apparatus according to claim 1, wherein the fiber sensor includes a fiber, and furthermore, detects a position of a source which generates a photoacoustic wave signal by using heterodyne signal.

8. The photoacoustic microscope apparatus according to claim 1, wherein the movable mirror is a galvanometer mirror which changes an angle of incidence of the excitation light on the objective lens by vibrations.

9. The photoacoustic microscope apparatus according to claim 2, wherein the movable mirror is a galvanometer mirror which changes an angle of incidence of the excitation light on the objective lens by vibrations.

10. The photoacoustic microscope apparatus according to claim 4, wherein the movable mirror is a galvanometer mirror which changes an angle of incidence of the excitation light on the objective lens by vibrations.

11. The photoacoustic microscope apparatus according to claim 1, wherein the movable mirror is a galvanometer mirror which changes an angle of incidence of the excitation light on the objective lens by vibrations.

12. The photoacoustic microscope apparatus according to claim 5, wherein the movable mirror is a galvanometer mirror which changes an angle of incidence of the excitation light on the objective lens by vibrations.

13. The photoacoustic microscope apparatus according to claim 6, wherein the movable mirror is a galvanometer mirror which changes an angle of incidence of the excitation light on the objective lens by vibrations.

14. The photoacoustic microscope apparatus according to claim 7, wherein the movable mirror is a galvanometer mirror which changes an angle of incidence of the excitation light on the objective lens by vibrations.

* * * * *